United States Patent [19]

Miyahara et al.

[11] Patent Number: 4,725,428
[45] Date of Patent: Feb. 16, 1988

[54] DENTAL CARIES-PREVENTIVE COMPOSITION CONTAINING ANTIBODY

[75] Inventors: Tsuneo Miyahara; Yoshihiro Harada, both of Kanagawa; Katsuyuki Futakami, Chigasaki, all of Japan

[73] Assignee: Lion Corporation, Tokyo, Japan

[21] Appl. No.: 795,526

[22] Filed: Nov. 6, 1985

[30] Foreign Application Priority Data

Nov. 6, 1984 [JP] Japan .................. 59-232352

[51] Int. Cl.$^4$ .................. A61K 7/26; A61K 7/16; A61K 7/22; A61K 7/28
[52] U.S. Cl. .................. 424/50; 424/49; 424/54; 424/58
[58] Field of Search .................. 424/49–50, 424/54, 58

[56] References Cited

U.S. PATENT DOCUMENTS 3,879,545  4/1975  Gaffar et al. .................. 424/50
3,931,398  1/1976  Gaffar et al. .................. 424/50
4,279,888  7/1981  Suganuma et al. .................. 424/50

FOREIGN PATENT DOCUMENTS 1505513  3/1978  United Kingdom .

OTHER PUBLICATIONS

Berkenbilt et al., *J. Amer. Dent. Association*, 83, 332–337, 1971.

Primary Examiner—J. R. Brown
Assistant Examiner—F. T. Moezie
Attorney, Agent, or Firm—Birch, Stewart, Kolasch & Birch

[57] ABSTRACT

There is provided a dental caries-preventive composition containing an antibody and a nonionic surface active agent, said antibody being obtained from an animal immunized with cells or cell components of *Streptococcus mutans*. The dental caries-preventive composition inhibits the formation of dental plaque and prevents dental caries. It keeps the antibody stable for a long period of time and hence permits the antibody to exhibit its effect with certainty over a long period of time.

16 Claims, No Drawings

DENTAL CARIES-PREVENTIVE COMPOSITION CONTAINING ANTIBODY

BACKGROUND OF THE INVENTION

The present invention relates to a dental caries-preventive composition which is contains an antibody obtained by the immunization of an animal with cells or cell components of *Streptococcus mutans*. More particularly, the present invention relates to a dental caries-preventive composition which keeps the antibody stable for a long period of time and hence permits the antibody to exhibit its effect with certainty over a long period of time, thereby inhibiting the formation of dental plaque and preventing dental caries.

Dental plaque firmly adhering to the surface of teeth is composed of about 70% bacteria, about 20% polysaccharides produced by the bacteria and about 10% food remains. It is said that acids stored in dental plaque decalcify enamel, causing dental caries. Therefore, dental plaque is observed as a cause of dental caries.

Formation of dental plaque is accelerated due to the synthesis of polysaccharides from sucrose by oral bacteria, especially *Streptococcus mutans*. In more detail, *Streptococcus mutans* synthesizes adhesive polysaccharides such as dextran and mutan from sucrose through the production of GTF (glucosyltransferase, dextran-synthesizing enzyme). The thus synthesized polysaccharides incorporate *Streptococcus mutans* as well as other bacteria and viruses, forming dental plaque having a given bacterial bouquet. In addition, bacteria such as *Streptococcus mutans* produce acids by utilizing various kinds of sugar and the thus produced acids decalcify the surface of enamel by remaining in polysaccharides and bacterial walls.

Accordingly, it is desirable to decrease the number of *Streptococcus mutans* in the mouth and suppress the formation of dental plaque in order to prevent dental caries.

It is known in British Pat. No. 1,505,513 that colonization of *Streptococcus mutans* in the mouth is suppressed by using mother's milk obtained by immunizing a cow with whole bacterial bodies of *Streptococcus mutans*.

The present inventors studied antibodies which are amongst the antibodies to various antigens derived from *Streptococcus mutans* and inhibit the colonization of *Streptococcus mutans* in the mouth. As a result, the inventors found that antibodies contained in antiserum and milk obtained by immunizing mammals with *Streptococcus mutans*, its cell-wall fraction, fibrous substance fraction, pilus component fraction, glucosyltransferase fraction and protein antigen fraction have a dental-plaque-formation suppressing effect. However, these antibodies are not stable in a dental caries-preventive composition, and particularly they become readily deactivated in the presence of an anionic surface active agent such as sodium lauryl sulfate. Thus it is necessary to incorporate the antibody into a dental caries preventive composition in such a manner that it remains effective for a long period of time.

SUMMARY OF THE INVENTION

Accordingly, it is an object of the present invention to provide a dental caries-preventive composition in which an antibody obtained from an animal immunized with cells or cell components of *Streptococcus mutans* is incorporated stably for a long period of time.

For the purpose of attaining the above object, the present inventors carried out research on the incorporation of a dental caries preventive composition with an antibody obtained from an animal immunized with cells or cell components of *Streptococcus mutans*. As the result, it was found that the antibody thus obtained is stable for a long period of time in a dental caries preventive composition containing an anionic surface active agent such as sodium lauryl sulfate, when the antibody is incorporated in the composition in combination with a nonionic surface active agent, particularly alkanolamide fatty acid ester such as lauroyl diethanolamide.

According to the present invention, therefore, there is provided a dental caries-preventive composition which comprises an antibody and a nonionic surface active agent, said antibody being obtained from an animal immunized with cells or cell components of *Streptococcus mutans*.

The dental caries preventive composition of this invention is applied in a proper form of preparation to the oral cavity. The antibody contained therein, which is obtained from an animal immunized with cells or cell components of *Streptococcus mutans*, prevents the colonization of *Streptococcus mutans* in the oral cavity and inhibits the formation of dental plaque. On account of a nonionic surface active agent incorporated in the composition, the antibody is not deactivated and keeps its effect for a long period of time.

The above and other objects, features, and advantages of this invention will be more fully understood from the following description.

DETAILED DESCRIPTION OF THE INVENTION

The dental caries preventive composition of this invention is incorporated with an antibody obtained from an animal immunized with cells or cell components of *Streptococcus mutans* as the antigen.

*Streptococcus mutans* used as an antigen may be prepared through well-known culture and pretreatment carried out by, for example, growing bacteria in external solution obtained by the dialysis of BHI medium before the thus grown bacteria are washed and subjected to formalin treatment. *Streptococcus mutans* separated from human mouth and belonging to the serotypes c, d, e, f and g may preferably be used, particularly one which is numerous in the human mouth belonging to the serotype-c. Such *Streptococcus mutans* includes NCTC10449, Ingbritt, OMZ70, JC-2, etc. and their mutant strains. Examples of preferred mutants include K-Dp strain (FERM-BP317), $KH_2$ strain (FERM-P7166), and K-III strain (Bikoken Deposit No. 6314).

The antigen to obtain the antibody used in this invention is cells or cell components of *Streptococcus mutans*, particularly the cell-wall fraction, fibrous structure fraction, pilus component fraction, glucosyltransferase (GTF) fraction, and protein antigen fraction of *Streptococcus mutans*.

The cell-wall fraction of *Streptococcus mutans* may be prepared, for example, according to the method of Bleiweis et al. (J. Bacteriol., 88, 1198–1200, 1964) by subjecting *Streptococcus mutans* to crushing treatment in a Brown's cell crusher and glass beads of 0.17 to 0.18 mm diameter, then treating the thus obtained cell walls with trypsin to remove protein contaminating the cell walls, followed by washing the cell walls with distilled water before they are lyophilized.

The fibrous (pili-like or fimbriae) substance fraction may be prepared, for example, according to the method of J. Van Hoate et al. (Arch. Oral. Bio., 16, 1131–1141, 1971) by culturing *Streptococcus mutans* in a medium obtained by the dialysis of BHI medium and containing 5% sucrose under an anaerobic condition, then centrifuging the culture medium to obtain a supernatant solution, then adding three times as much ethanol as the supernatant solution by volume, followed by collecting the precipitate of the thus obtained solution.

The pilus component fraction is obtained according to the process proposed by Tsurumizu et al. (Japanese Journal of Bacteriology, 38 (1) 471, 1983). According to this method, the pure structure fraction is prepared by the ordinary cell wall extraction method from cultured bacteria using a solvent such as phosphate buffer solution containing 1M salt. For example, to obtain the pilus component fraction of Streptococcus mutans, variant K-Dp, the strain is grown in a liquid medium and the culture medium is saturated (33%) with ammonium sulfate. The supernatant liquid is discarded and the precipitates are dispersed in a phosphate buffer solution (pH 7.0) containing 1M sodium chloride, followed by stirring at 4° C. for 3 days. The bacterial cells are removed by centrifugal separation, and the supernatant liquid is saturated (60%) with ammonium sulfate. The precipitates are dialyzed against phosphate buffer, and the dialyzate is subjected to sucrose density-gradient ultracentrifugal fractionation and the fraction at the sucrose density of 8 to 15% is collected. This fraction is dialyzed again against phosphate buffer to obtain the desired fraction.

The GTF fraction may be prepared, for example, according to the method of Inoue et al. (Microbial Aspects of Dental Caries Vol. III, 665–682, 1976 [Information Retrieval Inc.]) using a solution prepared by the following method: after *Streptococcus mutans* is implanted and grown in a medium obtained by the dialysis of BHI medium, the bacterial bodies are removed by centrifugation and the supernatant is saturated with ammonium sulfate at the level of 40%, followed by dialyzing the precipitate of the 40% ammonium sulfate fraction against 50 mM phosphate buffer solution and concentrating or diluting the obtained solution. The protein antigen fraction may be prepared, for example, according to the method of Lehner et al. (J. General Microbiology, 122, 217–225, 1981) by culturing *Streptococcus mutans* in a medium obtained by the dialysis of BHI medium and then centrifuging the culture medium to obtain a supernatant solution, followed by fractionation with 75% ammonium sulfate solution to collect the precipitate. The thus obtained precipitate is then subjected to DE-52 column chromatography under the existence of 6M urea, and the protein antigen fraction is dissolved in physiological saline, this being followed by dialyzing the thus obtained solution whereafter the dialyzed solution is subjected to gel filtration through Sepharose CL6B.

The usual method may be adopted in immunizing mammals with said antigens. As mammals to be immunized, goats, sheep, horses, cows, rabbits, etc. may be used.

In this invention, the antibody contained in the antiserum and milk obtained by immunizing the mammal with said antigen is blended into the composition. In this case, the antiserum and milk as well as the antibody separated and purified therefrom may be used. Each of these materials may be used alone or in a combination of two or more.

The antibody (protein fraction in the antiserum and the milk) may be separated from the antiserum and the milk according to the ordinary antibody purification method including the salting-out method, the gel-filtration method, ion-exchange chromatography, affinity chromatography, and the like, the salting-out method using ammonium sulfate being preferred. In the salting-out method, the antiserum or the milk is saturated with ammonium sulfate, preferably at the level of not more than 40%, to produce the precipitate, followed by dialyzing the precipitate against physiological saline to obtain the purified precipitate as the antibody. The preferred antibody is obtained from the equine antiserum and the bovine antiserum and milk.

The dose of an antibody may preferably be 0.0001 to 50 g/kg/day. To establish this dose, an antibody is incorporated in an amount of 0.0002 to 10% by weight, preferably 0.002 to 5% by weight, into a desired composition.

The dental caries-preventive composition of this invention contains, in addition to the above-mentioned antibody, a nonionic surface active agent to stabilize the antibody. It effectively prevents the antibody from becoming deactivated for a long period of time, even in the case where the composition contains an anionic surface active agent which easily deactivates the antibody.

The nonionic surface active agent includes alkanolamide fatty acid ester, sucrose fatty acid ester, polyoxyethylene sorbitan fatty acid ester, polyoxyethylene fatty acid ester, polyoxyethylene hardened castor oil derivative, lactose fatty acid ester, lactitol fatty acid ester, maltitol fatty acid ester, and polyoxyethylene-polyoxypropylene block copolymer. They may be used alone or in combination with one another. Preferable among them are alkanolamide fatty acid ester, sucrose fatty acid ester, polyoxyethylene sorbitan fatty acid ester, polyoxyethylene fatty acid ester, and polyoxyethylene hardened castor oil derivative, and most preferable is alkanolamide fatty acid ester.

Preferred alkanolamide fatty acid ester is one in which the fatty acid group has 9 to 18 carbon atoms and the alkanol group has 2 to 3 carbon atoms. The fatty acid may be a saturated one or an unsaturated one, and it may be of straight chain or branched chain. The fatty acid may be a mixed fatty acid. Examples of alkanolamide fatty acid ester include caproyl monoethanolamide, lauroyl diethanolamide, myristoyl diethanolamide, palmitoyl diethanolamide, diethanolamide coconut oil fatty acid ester, diethanolamide tallow fatty acid ester and lauroyl monoisopropanolamide. Preferable among them are lauroyl diethanolamide and myristoyl diethanolamide.

Preferred sucrose fatty acid ester is one which has a fatty acid group of carbon number 8 to 18 and has a degree of esterification of 0.8 to 3. It includes, for example, sucrose mono- and di-laurate.

Preferred polyoxyethylene sorbitan fatty acid ester is one which has a fatty acid group of carbon number 8 to 20, 6 to 60 mol of ethylene oxide added, and a degree of esterification of 1 to 3. It includes, for example, polyoxyethylene (20 mol) sorbitan monooleate, polyoxyethylene (6 mol) sorbitan monostearate, and polyoxyethylene (20 mol) sorbitan monolaurate.

Preferred polyoxyethylene fatty acid ester is one which has 1 to 60 mol of ethylene oxide added and a fatty acid of carbon number 8 to 20. It includes, for example, polyoxyethylene (60 mol) hardened castor oil, polyoxyethylene (10 mol) laurate, and polyoxyethylene (40 mol) stearate.

The amount of nonionic surface active agent in the dental caries-preventive composition may be 0.1 to 3% by weight, preferably 0.3 to 1.5% by weight of the composition.

The nonionic surface active agent prevents an antibody incorporated in the dental caries-preventive composition from becoming deactivated even in the case where the composition contains an anionic surface active agent which easily deactivates the antibody. Therefore, the dental caries-preventive composition can be effectively incorporated with anionic surface active agent including water-soluble salts of alkyl sulfate having 8 to 18 carbon atoms such as sodium lauryl sulfate and sodium myristyl sulfate, sodium salts of higher fatty acids, water-soluble salts of sulfonated monoglycerides of higher fatty acids having 10 to 18 carbon atoms in the fatty acid group such as sodium lauryl monoglyceride sulfonate and sodium coconut monoglyceride sulfonate, sodium monoglyceride monosulfates of higher fatty acids, α-olefin sulfonates, paraffin sulfonates, sodium N-methyl-N-palmitoyl touride, sodium N-lauroyl sarcosinate, sodium N-lauroyl-alanine. Among them, water-soluble salts of alkyl sulfate are preferable.

The amount of anionic surface active agent in the dental caries-preventive composition may be 0.5 to 3% by weight, preferably 1 to 2% by weight. The ratio of nonionic surface active agent to anionic surface active agent should be 0.4:1 to 3:1, preferably 1:1 to 1.5:1 by weight.

The dental caries preventive composition of this invention may be incorporated, in addition to the above-mentioned antibody, with at least one synergist selected from fluorine compound, chlorhexidine, lytic enzyme, bacteriocin, glucosyltransferase inhibitor, protease, and dextranase. They will inhibit the colonization of *Streptococcus mutans* and the formation of dental plaque, increasing the effect of dental caries prevention.

Examples of the fluorine compound include monofluorophosphates such as sodium monofluorophosphate, potassium monofluorophosphate, sodium hydrogen monofluorophosphate, and ammonium monofluorophosphate; alkali metal fluorides such as sodium fluoride, potassium fluoride, lithium fluoride, and ammonium fluoride; stannous-containing fluorides such as stannous fluoride; and other compounds such as potassium hexafluorozirconate, potassium hexafluorotitanate, cesium fluoride, nickel fluoride, zirconium fluoride, silver fluoride, hexylamine hydrofluoride, laurylamine hydrofluoride, cetylamine hydrofluoride, glycine hydrofluoride, lysine hydrofluoride, and alanine hydrofluoride. Preferable among them are monofluorophosphates such as sodium monofluorophosphate and potassium monofluorophosphate; alkali metal fluorides such as sodium fluoride, potassium fluoride, and ammonium fluoride; and stannous-containing fluorides such as stannous fluoride and stannous fluoride chloride. Most preferable are sodium monofluorophosphate, sodium fluoride, and stannous fluoride.

Examples of the chlorhexidine include chlorhexidine hydrochloride and chlorhexidine gluconate.

Examples of the lytic enzyme include those which are derived from *Streptomyces griseus*, *Streptomyces diastatochromagenes*, *Streptomyces farinosus*, Chalaropsis, Flavobacterium, Myxobacter, *Staphylococcus epidermidis*, Micrococcus, *Pseudomonas aeruginosa*, Aeromonas, *Streptomyces albus*, and *Streptomyces globisporus*.

Examples of the bacteriocin include those which are derived from *Enterobactor cloacae*, *Escherichia coli*, *Proteus miabilis*, *Pseudomonas aeruginosa*, *Streptococcus mutans*, and *Streptococcus staphylolyticus*.

Examples of the GTF inhibitor include those which are derived from Arthrinum sp., Fusarium sp., Macrophomina sp., Micromonospora sp., Gnomoniella sp., Nodulisporium sp., and Aspergillus sp. Specific examples that can be used are disclosed in Japanese Patent Laid-open Nos. 103193/1981, 28097/1982, 98215/1982, and 146587/1982.

Examples of the protease include those which are derived from Aspergillus sp. and Bacillus sp.

Examples of the dextranase include those which are derived from Chaetomium sp., Streptomyces sp., Bacillus sp., and Corynebacterium.

In this invention, the above-mentioned synergists may be used alone or in combination with one another. The above-mentioned antibody and synergist may be mixed together to make a composition of desired type or may be made into separate preparations which are put together at the time of use.

The dose of the synergist is as follows:

| | |
|---|---|
| Fluorine compound | 0.0001 to 1 g/kg/day |
| Chlorhexidines | 0.0001 to 1 g/kg/day as chlorhexidine |
| Lytic enzyme | 0.0001 to 10 g/kg/day |
| Bacteriocin | 0.0001 to 10 g/kg/day |
| GTF inhibitor | 0.0001 to 10 g/kg/day |
| Protease | 0.0001 to 5 g/kg/day |
| Dextranase | 0.0001 to 5 g/kg/day |

The amount of the synergist in each composition containing it is as follows:

| | |
|---|---|
| Fluorine compound | 0.0001 to 0.1 wt %, preferably 0.0001 to 0.001 wt %, in terms of fluorine |
| Chlorhexidine | 0.1 to 1000 ppm, preferably 10 to 100 ppm, in terms of chlorhexidine |
| Lytic enzyme | 0.0001 to 10 wt %, preferably 0.001 to 5 wt % |
| Bacteriocin | 0.0001 to 10 wt %, preferably 0.001 to 5 wt % |
| GTF inhibitor | 0.0001 to 10 wt %, preferably 0.001 to 5 wt % |
| Protease | 0.0001 to 10 wt %, preferably 0.001 to 5 wt % |
| Dextranase | 0.0001 to 10 wt %, preferably 0.001 to 5 wt % |

The caries-preventive composition according to this invention can be prepared and used in various forms applicable to the mouth such as dentifrices (including toothpaste, toothpowder and liquid dentifrice), mouthwashes, dental pastes, gingival massage creams, gargle tablets, troches, chewing gums, ice-creams, whipped creams and the like. The composition may further include additional well-known ingredients depending on the type and form of a particular composition. Any desired known ingredients may be mixed with said antibody and synergist component.

In preparing dentifrice compositions, an abrasive may be blended generally in an amount of 5 to 95%, especially 15 to 60% by weight of the composition, including calcium secondary phosphate dihydrate, calcium secondary phosphate anhydrate, calcium primary phosphate, calcium tertiary phosphate, calcium carbonate, calcium pyrophosphate, insoluble sodium metaphosphate, amorphous silica, crystal silica, aluminosilicate, aluminum oxide, aluminum hydroxide, magnesium tertiary phosphate, magnesium carbonate, calcium sulfate, titanium dioxide, resins, and the like.

Among them, aluminum hydroxide is preferable because of its stabilizing effect of the above-mentioned antibody. As aluminum hydroxide, a modified aluminium hydroxide which is obtained by surface treating aluminum hydroxide with phosphoric acid or its salt can be used.

In preparing paste-like compositions, typically toothpastes, a binder may be blended generally in an amount of 0.3 to 5% by weight, including sodium carboxymethyl cellulose, methyl cellulose, sodium carboxymethyl hydroxyethyl cellulose, hydroxyethyl cellulose, sodium alginate, carrageenan, gum arabic, xanthan gum, tragacanth gum, karaya gum, polyvinylalcohol, sodium polyacrylate, carboxyvinyl polymer, polyvinyl pyrrolidone, and the like.

Among them, carrageenan is preferred because it can stabilize the antibody.

In preparing paste-like and liquid compositions, typically toothpastes and mouthwashes, a humectant may be blended generally in an amount of 10 to 70% by weight, including polyethylene glycol, ethylene glycol, sorbitol, glycerol, propylene glycol, 1,3-butylene glycol, xylitol, maltitol, lactitol, and the like.

A flavor such as an essential oil including peppermint oil and spearmint oil and a flavoring material including l-menthol, carvone, eugenol and anethole, a sweetener such as sodium saccharinate, stevioside, neohesperidyldihydrochalcone, glycyrrhizin, perillartine, p-methoxycinnamic aldehyde, a preservative, and the like may be blended in an effective amount.

In this invention, effective ingredients such as mutanase, sorbic acid, alexidine, hinokitiol, cetylpyridinium chloride, alkyl glycine, alkyldiaminoethyl glycinate, allantoin, ξ-aminocaproic acid, tranexamic acid, azulene, vitamin E, a water soluble primary or secondary phosphate, a quaternary ammonium compound, sodium chloride and crude drugs may also be blended in an effective amount.

Further, the composition of this invention contain a protein such as gelatin, peptone, casein, collagen and albumin. These proteins can effectively stabilize the above-mentioned antibody. The blending amount of the protein may preferably be in the range of 0.001 to 10%, particulary 0.05 to 5% by weight of the composition.

Other types of compositions may also be prepared by selecting any desired ingredients as usual and mixing them by a conventional procedure.

Examples of the other ingredients for various types of forms of the composition are shown in the following Examples.

Paste-like and liquid oral compositions may generally have a pH ranging from 5 to 10, but not limited thereto.

The dental caries-preventive composition of this invention may be packaged in a proper container for storage and convenient use. In the case of toothpaste, it can be packaged in a plastic container such as plastic tube and aluminum foil laminate plastic tube or in a metal container such as aluminum tube. Usually the above-mentioned antibody is easily deactivated in a metal container; but the dental caries-preventive composition of this invention can be packaged in a metal container such as aluminum tube owing to a nonionic surface active agent incorporated therein which prevents the antibody from being deactivated in a metal container.

The dental caries-preventive composition of this invention is applied in a proper form of preparation to the oral cavity. The antibody contained therein, which is obtained from an animal immunized with cells or cell components of *Streptococcus mutans*, prevents the colonization of *Streptococcus mutans* in the oral cavity and inhibits the formation of dental plaque. On account of a nonionic surface active agent incorporated in the composition, the antibody is not deactivated and keeps its effect for a long period of time.

Examples of this invention will be given below although this invention is not restricted to them.

EXAMPLE 1

Antisera and mother's milks were obtained by using the following antigens according to the following method.

(1) Antigens

*Streptococcus mutans* NCTC10449

Bacteria grown in the external solution obtained by the dialysis of BHI medium, after being washed, were treated with formalin before being supplied for use.

Cell-wall fraction of *Streptococcus mutans* NCTC10449

The fraction prepared according to the method of Bleiweis et al. (J. Bacteriol., 88, 1198-1200, 1964) was supplied for use.

Fibrous substance fraction of *Steptococcus mutans* NCTC10449

The fraction prepared according to the method of J. Van Hoate et al. (Arch. Oral. Bio. 16, 1131-1141, 1971) was supplied for use.

Pilus component fraction of *Streptococcus mutans* NCTC10449

The fraction prepared according to the method of Tsurumizu et al. (Japanese Journal of Bacteriology, 38 (1), 471, 1983) was supplied for use.

Glucosyltransferase fraction of *Streptococcus mutans* NCTC10449

The fraction prepared according to the method of Inoue et al. (Microbial Aspects of Dental Caries Vol. III, 665-682, 1976 [Information Retrieval Inc.]) was supplied for use.

Protein antigen fraction of *Streptococcus mutans* NCTC10449

The fraction prepared according to the method of Lehner et al. (J. General Microbiology, 122, 217-225, 1981) was supplied for use.

(2) Preparation of antiserum, milk, and antibody

A mixture of 50 to 100 µg/ml of antigen and an equal amount of complete Freund's adjuvant was injected subcutaneously on the back of a pregnant goat, horse, cow, or rabbit at a dose of 0.3 ml per kg of weight. Then immunization was repeated in the same way as above with a mixture of antigen and incomplete Freund's adjuvant at intervals of 2 to 4 weeks. After delivery, colostrum was collected. On the other hand, to obtain antiserum, blood was collected from the animals which had undergone immunization four times in the same manner as above, and the blood was coagulated and supernatant liquid was centrifugally separated.

The colostrum mentioned above, with an equal amount of 0.9% salt solution added, was centrifuged at 15000 rpm for 60 minutes. Fat in the upper layer and precipitates were discarded and the liquid component in the middle layer was collected. It was adjusted to pH 4 with conc. hydrochloric acid. The resulting solution was centrifuged again at 5000 rpm for 30 minutes, and the supernatant liquid was neutralized with trishydroxyaminomethane and 75% saturated with ammonium sulfate. The resulting precipitates were collected and dialyzed against phosphate buffer solution, whereby there was obtained an antibody component of milk (inner solution).

The above-mentioned antiserum was 50% saturated with ammonium sulfate, and the resulting precipitates were dialyzed against phosphate buffer, whereby there was obtained an antibody of antiserum (inner solution).

[Experiment 1]

A solution containing 2.5% of the surface active agent shown in Table 1 and 10% of antibody (horse, S. mutans, strain 10449, pilus component) was stored at 40° C. for 1 week, and the residual antibody activity was measured in the following manner. Table 1 shows the results expressed in terms of index, with 100 being the antibody activity without surface active agent.

Measurement of Antibody Activity

Add 4 ml of phosphate buffer (0.1M, pH 7) to 1 g of sample so that the soluble components in the sample are dissolved in the buffer. Centrifuge the solution and collect the supernatant liquid. Measure the activity of the antibody in the supernatant liquid by using the cells of Streptococcus mutans, variant K-Dp, as the antigen according to ELISA method (Eng wall E. et al., J. Immunol., 109: 129–135, 1972). Determine the absorbance at 405 nm.

TABLE 1

| Surface active agent | Antibody activity |
| --- | --- |
| — | 100 |
| Sucrose monolaurate | 90 |
| POE (20) sorbitan monolaurate | 85 |
| POE (6) hardened castor oil | 94 |
| Lauroyl diethanolamide | 95 |
| Sodium N—lauroylglutamate | 80 |
| Sodium N—lauroylsarcosinate | 30 |
| Sodium lauryl sulfate | 20 |

[Experiment 2]

Toothpaste of the following formulation was prepared:

| | |
| --- | --- |
| Aluminum hydroxide | 43% |
| 60% sorbit solution | 35 |
| Propylene glycol | 3.0 |
| Carrageenan | 1.0 |
| Gelatin | 0.3 |
| Saccharin sodium | 0.1 |
| Flavor | 1.0 |
| Sodium monofluorophosphate | 0.76 |
| Methylparaben | 0.2 |

-continued

| | |
| --- | --- |
| Butylparaben | 0.01 |
| Sodium lauryl sulfate | 0.8 |
| Nonionic surface active agent | As shown in Table 2 |
| Rabbit anti S. mutans, K-Dp, cell wall serum | 0.5 |
| Water | Balance |
| | 100.0 |

The toothpaste was stored at 40° C. for 2 weeks and the residual antibody activity was measured in the same manner as in Experiment 1. Table 2 shows the results in terms of index, with 100 being the antibody activity of the toothpaste containing 1.5% of lauroyl diethanolamide.

TABLE 2

| Nonionic surface active agent | | Antibody activity |
| --- | --- | --- |
| Name | Amount | |
| Lauroyl diethanolamide | 1.5% | 100 |
| Lauroyl diethanolamide | 1.0 | 95 |
| Lauroyl diethanolamide | 0.8 | 90 |
| Lauroyl diethanolamide | 0.3 | 75 |
| — | — | 20 |
| Sucrose monolaurate | 1.0 | 90 |
| POE (20) sorbitan monolaurate | 1.0 | 85 |
| POE (60) hardened castor oil derivative | 1.0 | 95 |

[Experiment 3]

Toothpaste of the following formulation was prepared:

| | |
| --- | --- |
| Abrasive | As shown in Table 3 |
| 60% sorbit solution | 35% |
| Propylene glycol | 3.0 |
| Carrageenan | 1.0 |
| Gelatin | 0.3 |
| Saccharin sodium | 0.1 |
| Flavor | 1.0 |
| Sodium monofluorophosphate | 0.76 |
| Methylparaben | 0.2 |
| Butylparaben | 0.01 |
| Sodium lauryl sulfate | 0.8 |
| Lauroyl diethanolamide | 1.0 |
| Rabbit anti S. mutans, K-III, cell wall serum | 0.5 |
| Water | Balance |
| | 100.0 |

The toothpaste was stored at 40° C. for 2 weeks and the residual antibody activity was measured in the same manner as in Experiment 1. Table 3 shows the results in terms of index, with 100 being the antibody activity of the toothpaste containing 45% of aluminum hydroxide.

TABLE 3

| Abrasive | | Antibody activity |
| --- | --- | --- |
| Name | Amount | |
| Aluminum hydroxide | 45% | 100 |
| Calcium secondary phosphate dihydrate | 45 | 70 |
| Calcium carbonate | 43 | 70 |
| Silicic anhydride | 25 | 65 |

[Experiment 4]

Toothpaste of the following formulation was prepared:

| | |
|---|---|
| Aluminum hydroxide | 43% |
| 60% sorbit solution | 35 |
| Propylene glycol | 3.0 |
| Carrageenan | 1.0 |
| Protein or amino acid | 0.3 |
| Saccharin sodium | 0.1 |
| Flavor | 1.0 |
| Sodium monofluorophosphate | 0.76 |
| Methylparaben | 0.2 |
| Butylparaben | 0.01 |
| Sodium lauryl sulfate | 0.8 |
| Lauroyl diethanol amide | 1.0 |
| Horse anti S. mutans, 10449 strain, pilus component serum | 0.5 |
| Water | Balance |
| | 100.0 |

The toothpaste was stored at 40° C. for 2 weeks and the residual antibody activity was measured in the same manner as in Experiment 1. Table 4 shows the results in terms of index, with 100 being the antibody activity of the toothpaste containing peptone.

TABLE 4

| Protein or amino acid | Antibody activity |
|---|---|
| Peptone | 100 |
| Gelatin | 95 |
| Casein | 90 |
| Collagen | 90 |
| Albumin | 85 |
| Arginine | 30 |
| Glutamic acid | 35 |
| — | 20 |

[Experiment 5]

Toothpaste of the following formulation was prepared:

| | |
|---|---|
| Aluminum hydroxide | 43% |
| 60% sorbit solution | 35 |
| Propylene glycol | 3.0 |
| Binder | 1.0 |
| Gelatin | 0.3 |
| Saccharin sodium | 0.1 |
| Flavor | 1.0 |
| Sodium monofluorophosphate | 0.76 |
| Methylparaben | 0.2 |
| Butylparaben | 0.01 |
| Sodium lauryl sulfate | 0.8 |
| Lauroyl diethanolamide | 1.0 |
| Horse anti S. mutans, 10449 strain, pilus component serum | 0.5 |
| Water | Balance |
| | 100.0 |

The toothpaste was stored at 40° C. for 2 weeks and the residual antibody activity was measured in the same manner as in Experiment 1. Table 5 shows the results in terms of index, with 100 being the antibody activity of the toothpaste containing 1.5% of carrageenan.

TABLE 5

| Binder | Antibody activity |
|---|---|
| Carrageenan | 100 |
| Sodium alginate | 70 |
| Xanthane gum | 75 |
| Sodium carboxymethylcellulose | 70 |

EXAMPLE 2

(Toothpaste)

| | |
|---|---|
| Propylene glycol | 3.0% |
| Sodium alginate | 0.9 |
| Methylparaben | 0.2 |
| Butylparaben | 0.01 |
| Sodium benzoate | 0.1 |
| 60% sorbit solution | 35.0 |
| Saccharin sodium | 0.15 |
| Sodium monofluorophosphate | 0.76 |
| Dextranase (2,000,000 unit/g) | 0.1 |
| Gelatin | 0.3 |
| Sodium lauryl sulfate | 0.8 |
| Lauroyl diethanolamide | 1.0 |
| Flavor | 0.6 |
| Aluminum hydroxide | 45.0 |
| Horse anti-S. mutans, 10449, pilus component antibody | 0.1 |
| Purified water | Balance |
| | 100.0 |

EXAMPLE 3

(Toothpaste)

| | |
|---|---|
| Propylene glycol | 3.0% |
| Sodium carboxymethylcellulose | 1.2 |
| Methylparaben | 0.2 |
| Butylparaben | 0.01 |
| Sodium benzoate | 0.1 |
| 60% sorbit solution | 30.0 |
| Saccharin sodium | 0.2 |
| Stannous fluoride | 0.41 |
| Chlorhexidine hydrochloride | 0.01 |
| Peptone | 0.2 |
| Casein | 0.1 |
| Sodium lauryl sulfate | 0.8 |
| Sucrose monolaurate | 1.0 |
| Flavor | 0.6 |
| Aluminum hydroxide | 45.0 |
| Cow anti-S. mutans, 6715, GTF antibody | 0.2 |
| Purified water | Balance |
| | 100.0 |

EXAMPLE 4

(Toothpaste)

| | |
|---|---|
| Propylene glycol | 2.5% |
| Carrageenan | 0.8 |
| Methylparaben | 0.2 |
| Butylparaben | 0.01 |
| Sodium benzoate | 0.1 |
| 60% sorbit solution | 15.0 |
| 85% glycerin solution | 10.0 |
| Saccharin sodium | 0.15 |
| Sodium fluoride | 0.21 |
| Collagen | 0.2 |
| Albumin | 0.2 |
| Sodium lauryl sulfate | 0.8 |
| Polyoxyethylene (20 mol) sorbitan monooleate | 0.8 |
| Flavor | 0.6 |
| Calcium secondary phosphate | 40.0 |
| Sheep anti-S. mutans, Ingbritt, protein antigen | 0.05 |

-continued

| | |
|---|---|
| antibody | |
| Purified water | Balance |
| | 100.0 |

EXAMPLE 5

(Toothpaste)

| | |
|---|---|
| Propylene glycol | 2.5% |
| Carrageenan | 1.0 |
| Methylparaben | 0.2 |
| Butylparaben | 0.01 |
| Sodium benzoate | 0.1 |
| 85% glycerin solution | 21.0 |
| Saccharin sodium | 0.2 |
| Sodium monofluorophosphate | 0.76 |
| Chlorhexidine gluconate | 0.01 |
| Sodium lauryl sulfate | 0.8 |
| Sodium lauroyl sarcosinate | 0.2 |
| Polyoxyethylene (60 mol) hardened castor oil | 0.8 |
| Flavor | 0.6 |
| Abrasive silica | 35.0 |
| Rabbit anti-*S. mutans*, K-Dp, pilus component antibody | 0.5 |
| Purified water | Balance |
| | 100.0 |

EXAMPLE 6

(Mouthwash)

| | |
|---|---|
| Sodium lauryl sulfate | 0.8% |
| Lauroyl diethanolamide | 0.8 |
| Gelatin | 1.0 |
| Arginine | 0.1 |
| Potassium primary phosphate | 0.082 |
| Sodium secondary phosphate | 0.5 |
| Chlorhexidine gluconate | 0.01 |
| Goat anti-*S. mutans*, KH2, cell wall antibody | 0.1 |
| Glycerin | 12.0 |
| Flavor | 0.8 |
| Saccharin sodium | 0.2 |
| Purified water | Balance |
| | 100.0 |

EXAMPLE 7

(Mouthwash)

| | |
|---|---|
| Sodium lauryl sulfate | 0.8% |
| Sucrose monomyristate | 1.0 |
| Peptone | 1.0 |
| Potassium primary phosphate | 0.082 |
| Sodium secondary phosphate | 0.5 |
| Chlorhexidine gluconate | 0.01 |
| Horse anti-*S. mutans*, K-III, pilus component antibody | 0.05 |
| Glycerin | 12.0 |
| Flavor | 0.8 |
| Saccharin sodium | 0.2 |
| Purified water | Balance |
| | 100.0 |

EXAMPLE 8

(Mouthwash)

| | |
|---|---|
| Sodium lauryl sulfate | 0.8% |
| Polyoxyethylene (40 mol) monostearate | 1.2 |
| Albumin | 0.2 |
| Collagen | 0.2 |
| Casein | 6.2 |
| Arginin | 0.1 |
| Sodium secondary phosphate | 1.25 |
| Citric acid | 0.88 |
| Chlorhexidine gluconate | 0.01 |
| Sodium fluoride | 1.1 |
| Horse anti-*S. mutans*, OMZ176, pilus component antibody | 0.02 |
| Sorbit | 15.0 |
| Flavor | 0.8 |
| Saccharin sodium | 0.2 |
| Purified water | Balance |
| | 100.0 |

To be diluted 10 times with water when used.

EXAMPLE 9

(Mouthwash)

| | |
|---|---|
| Polyoxyethylene (60 mol) hardened castor oil | 1.5% |
| Sodium lauryl sulfate | 0.8 |
| Carrageenan | 0.01 |
| Sodium secondary phosphate | 1.25 |
| Citric acid | 0.88 |
| Chlorhexidine gluconate | 0.01 |
| Sodium monofluorophosphate | 3.8 |
| Rabbit anti-*S. mutans*, LM7, pilus component antibody | 0.01 |
| Sorbit | 15.0 |
| Flavor | 0.8 |
| Saccharin sodium | 0.2 |
| Purified water | Balance |
| | 100.0 |

To be diluted 10 times with water when used.

What is claimed is:

1. A dental composition, comprising:
   an effective amount to inhibit the colonization of *Streptococcus mutans* in the mouth of an antibody against a strain or mutant of human *Streptococcus mutans* serotype c, d, e, f or g; and
   an effective amount to stabilize said antibody of a nonionic surface active agent selected from the group consisting of alkanolamide fatty acid esters having 9 to 18 carbon atoms in the fatty acid group and 2 to 3 carbon atoms in the alkanol group, sucrose fatty acid esters having 8 to 18 carbon atoms in the fatty acid group and a degree of esterification of 0.8 to 3, polyoxyethylene sorbitan fatty acid esters having 8 to 20 carbon atoms in the fatty acid group, 6 to 60 mol of ethylene oxide added and a degree of esterification of 1 to 3, polyoxyethylene fatty acid esters having 8 to 20 carbon atoms in the fatty acid group 1 to 60 mol of ethylene oxide added and mixtures thereof.

2. The composition of claim 1, wherein said antibody is against a strain or mutan of human *Streptococcus mutans* serotype-c.

3. The composition of claim 1, which is in the form of a toothpaste.

4. The composition of claim 3, which includes aluminum hydroxide as a main abrasive.

5. The composition of claim 1, which includes carrageenan as a binder.

6. The composition of claim 1, which includes gelatin, peptone, casein, collagen or albumin.

7. A dental composition, comprising:
0.0002 to 10% by weight, based on the weight of the composition, or an antibody obtained by immunizing an antibody producing mammal with cells or a mutant of human *Streptococcus mutans* serotype c, d, e, f or g or antigenic cell components thereof selected from the group consisting of cell wall fraction, fibrous structure fraction, pilus component fraction, glucosyltransferase fraction and protein antigen fraction; and
0.1 to 3% by weight, based on the weight of the composition, of a nonionic surface active agent selected from the group consisting of alkanolamide fatty acid esters having 9 to 18 carbon atoms in the fatty acid group and 2 to 3 carbon atoms in the alkanol group, sucrose fatty acid esters having 8 to 18 carbon atoms in the fatty acid group and a degree of esterification of 0.8 to 3, polyoxyethylene sorbitan fatty acid esters having 8 to 20 carbon atoms in the fatty acid group, 6 to 60 mol of ethylene oxide added and a degree of esterification of 1 to 3, polyoxyethylene fatty acid esters having 8 to 20 carbon atoms in the fatty acid group and 1 to 60 mol of ethylene oxide added and mixtures thereof.

8. The composition of claim 7, wherein said antibody producing mammal is a goat, sheep, horse, cow or rabbit.

9. The composition of claim 7, wherein the mutant is variant K-Dp, KH2, or K-III of *Streptococcus mutans*.

10. The composition of claim 17, which further comprises an anionic surface active agent.

11. The composition of claim 10, wherein the ratio of nonionic surface active agent to anionic surface active agent is 0.4:1 to 3:1 by weight.

12. The composition of claim 10, wherein the anionic surface active agent is a water-soluble salt of alkyl sulfate.

13. The composition of claim 7, which is in the form of a toothpaste or mouthwash.

14. The composition of claim 7, which includes aluminum hydroxide as a main abrasive.

15. The composition of claim 7, which includes carrageenan as a binder.

16. The composition of claim 7, which includes gelatin, peptone, casein, collagen or albumin.

* * * * *